US00PP13721P39

(12) United States Plant Patent
Zerr

(10) Patent No.: US PP13,721 P3
(45) Date of Patent: Apr. 8, 2003

(54) POINSETTIA PLANT NAMED 'FISSON JINGLIT'

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/880,877

(22) Filed: Jun. 15, 2001

(65) Prior Publication Data

US 2002/0194663 P1 Dec. 19, 2002

(51) Int. Cl.[7] ..... A01H 5/00

(52) U.S. Cl. ..... Plt./303

(58) Field of Search ..... Plt./303

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of Poinsettia plant named 'Fisson Jinglit', as described and illustrated, and particularly characterized by the combined features of bright-red colored bracts with numerous, small white spots; medium sized inflorescence with distinctly pointed bracts; uniform, dark-green foliage with relatively strong pointed lobes; relatively compact, bushy and round plant habit; and medium flower response.

1 Drawing Sheet

LATIN NAME OF THE GENUS AND SPECIES OF THE PLANT CLAIMED

*Euphorbia pulcherrima.*

VARIETY DENOMINATION

Fisson Jinglet

BACKGROUND OF THE INVENTION

The present invention relates to a new and distinct cultivar of poinsettia plant known by the cultivar name 'Fisson Jinglit', and botanically known as *Euphorbia pulcherrima.*

'Fisson Jinglit' originated from a naturally occurring mutation in the variety 'Fisson Jingle' (U.S. Plant Pat. No. PP 12,540), which was discovered by the inventor, Katharina Zerr, in a greenhouse in Hillscheid, Germany, among a group of flowering pot plants in the fall of 1997.

Shoot tip cuttings were taken from the mutated part of the plant in the spring of 1998. The plants grown from these cuttings were examined and selected for uniformity in the fall of 1998. The remaining plants were multiplied once more and the plants grown thereof proved to be uniform in an examination in late summer to fall 1999.

Horticultural examination of 'Fisson Jinglit' starting in 1999 and continuing thereafter has demonstrated/confirmed that the combination of characteristics as herein disclosed for 'Fisson Jinglit' are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Fisson Jinglit' which in combination distinguish this Poinsettia as a new and distinct cultivar:

1. bright-red colored bracts with numerous, small white spots;

2. medium sized inflorescence with distinctly pointed bracts;
3. uniform, dark-green foliage with relatively strong pointed lobes;
4. relatively compact, bushy and round plant habit; and
5. medium flower response.

'Fisson Jinglit' has not been observed under all possible environmental conditions. The phenotype may vary significantly with variations in environment such as temperature, light intensity, and daylength. The following observations, measurements and comparisons describe plants grown in Hillscheid, Germany, under greenhouse conditions which approximate those generally used in commercial practice.

Of the may commercial cultivars known to the inventor, the most similar in comparison to 'Fisson Jinglit' is the patented cultivar 'Fisson' (U.S. Plant Pat. No. 9,365), and the parental cultivar 'Fisson Jingle', (U.S. Plant patent application Ser. No. 09/099,775).

In comparison to the uniform red colored variety 'Fisson', 'Fisson Jinglit' has a variegated bract color, there are numerous white spots spread over the surface. Furthermore, 'Fisson Jinglit' has a more compact plant habit, and its plants are smaller by about 20%.

In comparison to 'Fisson Jingle', 'Fisson Jinglit' has a similar red main bract color and a similar type of variegation, however with white spots instead of pink ones. The variegation, however, is more uniform with respect to the size of the spots and there is less tendency to developing deviations from the usual pattern. Additionally, plants of 'Fisson Jinglit' are slightly smaller than those of 'Fisson Jingle'.

BRIEF DESCRIPTION OF THE DRAWING

The accompanying color photographic drawing shows typical inflorescence and foliage of 'Fisson Jinglit', with colors being as true as possible with illustrations of this type. The photograph shows a mature potted plant.

DETAILED BOTANICAL DESCRIPTION

The plants described were grown in a greenhouse in Hillscheid, Germany, in the fall of 2000. Rooted cuttings had been planted into 12 cm pots on August 10, and were pinched 12 days later, leaving 8 nodes. The minimum temperature was about 20° C. until the end of September, and about 17–18° C. thereafter. The plants initiated flowers under natural short-day conditions in fall.

Observations and measurements were mainly taken at the beginning of full flowering. In the following description color references are made to The Royal Horticultural Society Colour Chart (R.H.S.). The color values were determined indoors in a north light.

Plant:

*Form.*—Shrub, self-branching.

*Growth habit.*—Moderately compact, and free branching, pinched plants are bushy and round in shape.

*Height* (*above soil line*).—24.0 cm.

*Width.*—33.0 cm.

*Average number of branches.*—8.1.

*Average length of branches.*—16–19 cm.

*Average internode length.*—18–23 mm.

*Average number of inflorescence.*—7.

*Stem color.*—Mainly green, RHS 143 A, a slight reddish infusion may occur in parts.

*Rooting.*—Medium, about 20 days.

*Blooming habit.*—Begin under natural short day conditions in fall; botanically (cyathia open) in early December; commercially (bracts colored, marketable) in early December.

*Flowering response time.*—Approximately 9.5 weeks.

*Flowering season.*—Up to approximately 4 weeks.

*Keeping quality* (*shelf life*).—Relatively good, about 28 days.

Foliage:

*Shape.*—Roughly ovate with acute or obtuse base, acuminate tip, and most often with strong, pointed lobes, smaller leaves without lobes are broad elliptically shaped.

*Leaf arrangement.*—Alternate.

*Margin.*—Entire.

*Texture.*—Upper surface: smooth and flat, only weakly veined, color of the veins near the base of the midrib RHS 180 A. Lower surface: flat and smooth, except for the slightly protruding midrib and finer side veins, in a palmate pattern, the vein color is brownish pink RHS 180 C or lighter.

*Size.*—Leaf blade length 9.5 cm, width 8,5 cm; petiole length 6.8 cm.

*Color.*—Generally dark-green, uniform.

*Mature foliage.*—Upper surface RHS 139 A; under surface RHS 139 B.

*New foliage.*—Upper side RHS 137 A; under side RHS 137 C.

*Leaf petiole.*—Upper side RHS 60 A, lower side RHS 180 A to 180 B, with one or two narrow green lines.

*Aspect.*—Most often the petioles are slightly upward directed, while the leaf blades show downward.

Disease resistance: No special observations made.

Flowering description: Whole inflorescence with surrounding bracts: up to medium sized, almost flat circle with the larger bracts horizontally or slightly downward directed, while young bracts show initially somewhat upwards; average inflorescence height 25–35 mm.

*Diameter.*—18–19 cm.

*Number of bracts per inflorescence.*—9–12.

*Bract shape.*—Larger bracts are roughly ovate, with acute bases and acuminated tips, and distinctly lobed with pointed tips; the smaller upper bracts are broad elliptically shaped and usually without lobes.

*Texture surface.*—Smooth and flat, with the veins hardly visible; as bracts mature, veins create a more rugose pattern similar to the foliage leaves.

*Vein color.*—Lower surface is reddish pink, approximately RHS 51 A or slightly darker.

*Color.*—Generally a bright medium red upper surface, main color RHS 45 A to 45 B; upper surface spots cream colored, RHS 4 D; lower surface main color red RHS 46 B; lower surface spots cream RHS 4 D.

*Petiole color.*—Red slightly darker than RHS 46 B.

*Cyme.*—Approximately 5–10 cyathia in a narrow cluster, retention medium.

*Cyathium.*—Approximately 45–50 mm wide, 13–15 mm long (including peduncle and stamen); color: light green, RHS 143 B, top reddish; one nectary per cyathium. Nectar Cups: Intense yellow, RHS 7, no anthocyanin.

Reproductive organs:

*Stamens.*—Quantity: about 15 in a bundle; anther length about 4 mm; filiform shape; dark red filaments; yellow pollen; pollen quantity: moderate.

*Ovaries.*—Grass-green approximately RHS 143 A, triangular, 3 ovules.

Fruit/seed set: No seed set observed, but most probably fertile.

I claim:

1. A new and distinct cultivar of Poinsettia plant named 'Fisson Jinglit', as described and illustrated herein.

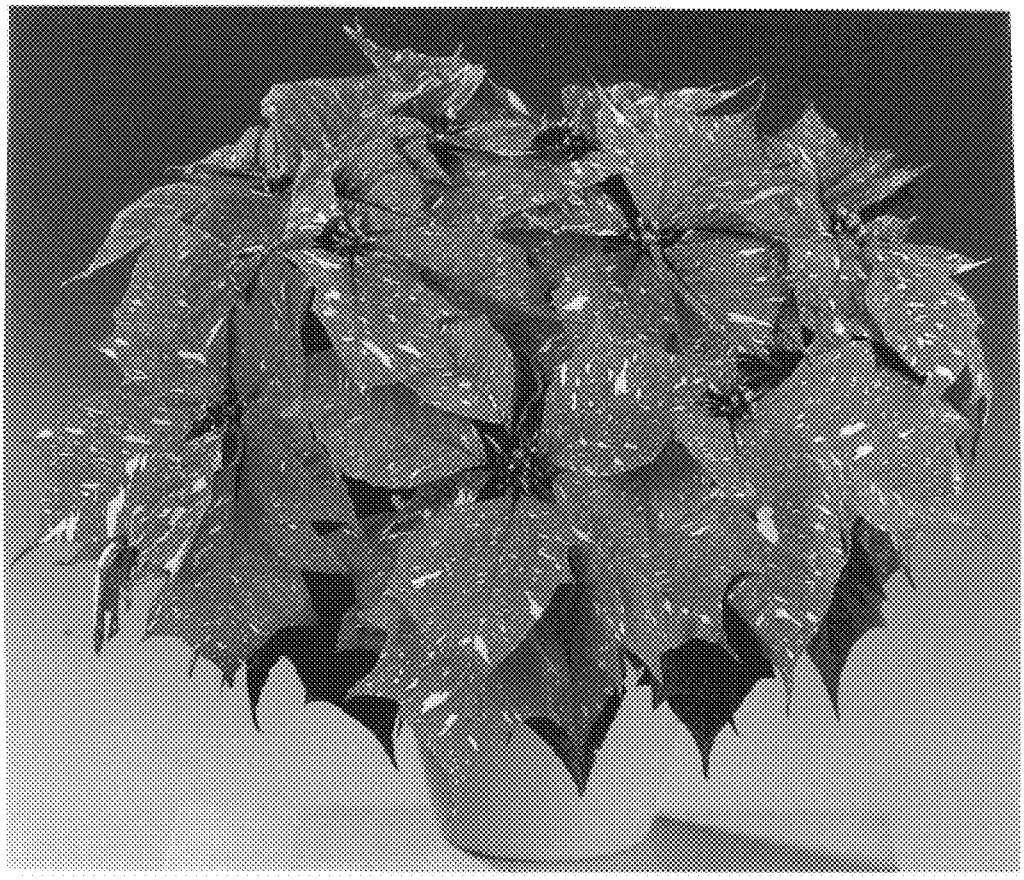

* * * * *